United States Patent [19]
Durr et al.

[11] Patent Number: 5,997,889
[45] Date of Patent: Dec. 7, 1999

[54] HAND AND BODY CREME FOR THE TREATMENT OF SKIN AILMENTS

[75] Inventors: Norma Jean Holloway Durr, Michigan City, Ind.; Crystal Elaine Porter; Curtis Philip Porter, both of Rolla, Mo.

[73] Assignee: Omnipotent Skin Products, L.L.C., Rolla, Mo.

[21] Appl. No.: 09/027,003

[22] Filed: Feb. 20, 1998

[51] Int. Cl.⁶ .............................. A61K 7/00; A61K 7/48; A61K 7/40
[52] U.S. Cl. ........................ 424/401; 514/458; 514/725; 514/844
[58] Field of Search ............................ 424/401; 514/458, 514/725, 844

[56] References Cited

U.S. PATENT DOCUMENTS 4,946,832  8/1990  Goode et al. .

FOREIGN PATENT DOCUMENTS

| 638 399 | 6/1993 | Australia . |
| 2 663 848 | 1/1992 | France . |
| 29 607 806 | 7/1996 | Germany . |
| 60 061 513 | 4/1985 | Japan . |
| 2 093 138 | 10/1997 | Russian Federation . |
| 822 824 | 4/1981 | U.S.S.R. . |

OTHER PUBLICATIONS

Flick, Cosmetic and Toiletry Formulations, vol. 2 (2d ed. 1992).

*Primary Examiner*—Thurman K. Page
*Assistant Examiner*—Brian K. Seidleck
*Attorney, Agent, or Firm*—Armstrong Teasdale LLP

[57] ABSTRACT

Compositions for a hand and body creme made substantially of naturally occurring ingredients are described. Such compositions are highly effective in clearing eczema and other common skin ailments. One embodiment, in which the hand and body creme is a creamy solid, is made by forming an admixture of cocoa butter, almond oil, jojoba oil, vitamin E oil, a commercially available beeswax derivative, hydrogenated soybean flakes, pure beeswax and vitamin A oil. In alternate embodiments, water, shea butter and honey are added to vary the consistency and moisturizing properties of the composition. In still other embodiments, essential oils from a variety of plant sources are added for a range of fragrances.

17 Claims, No Drawings

HAND AND BODY CREME FOR THE TREATMENT OF SKIN AILMENTS

FIELD OF THE INVENTION

This invention relates generally to topically applied compositions for the treatment and relief of skin ailments such as itching, dryness, eczema, psoriasis and rashes, and more particularly, to hand and body creme compositions comprising admixtures of naturally occurring ingredients.

BACKGROUND OF THE INVENTION

Skin ailments such as itchiness, dryness, eczema, psoriasis and rashes are a source of irritation for many individuals. The cosmetic and pharmaceutical industries offer a range of topically applied cremes, lotions and other like products for the treatment and relief of such common skin ailments. These products typically contain oils, waxes, or colloidal solids which act as skin emollients, therapeutic additives such as vitamin oils or zinc, and synthetic ingredients such as organic surfactants and preservatives. Such compositions provide easy-to-use and quick relief for certain ailments such as itchiness, dryness and rash. However, these compositions typically lack any long-lasting therapeutic effect in the treatment of skin ailments such as eczema and psoriasis. Additionally, some of the synthetic ingredients cause adverse reactions in users with sensitive skin, and some of the synthetic ingredients, such as formaldehyde, are known or suspected carcinogens. It would be desirable to provide a topically applied composition for the treatment and relief of eczema, psoriasis and other common skin conditions, which is made substantially of naturally occurring ingredients.

Other known products for the therapeutic treatment of skin conditions such as eczema and psoriasis contain tar derivatives such as whole coal tar or pine tar in an emollient base. Products containing tar derivatives may cause permanent staining of plastic and fiberglass materials, discoloration of color-treated hair, eye irritation, and allergic irritations. A need persists for a topically applied composition which is highly effective in the treatment and relief of eczema and psoriasis, as well as common ailments such as dryness and itching, yet is free of tar derivatives.

SUMMARY OF THE INVENTION

These and other objects may be attained by a composition for a hand and body creme which is highly effective in treating eczema and other common skin ailments, and by a method for making such a composition primarily from naturally occurring substances. In one embodiment, the composition for the hand and body creme is an admixture of almond oil, cocoa butter, jojoba oil, vitamin E oil, a commercially available beeswax derivative, hydrogenated soybean flakes, pure beeswax and vitamin A oil.

One embodiment of the hand and body creme composition is prepared by melting the cocoa butter, a beeswax derivative, and pure beeswax, and combining them at a temperature of about 128° F. to about 132° F. The hydrogenated soybean flakes are then added to the hot wax mixture. Separately, the almond oil, jojoba oil, vitamin E oil and vitamin A oil are combined at room temperature to form an oil mixture. The hot wax mixture is transferred to a blender and blended at high speed under vacuum. The oil mixture is then introduced to the wax mixture in the blender and blended at high speed under vacuum. The entire mixture is then poured into opaque storage containers and cooled at a room temperature of less than 85° F. to form a cream-colored solid which may be topically applied to skin on hands and body.

In alternate embodiments, essential oils from a variety of plant sources are added for a range of fragrances. In still other embodiments, water, shea butter and honey are added to vary the consistency and moisturizing properties of the composition.

The hand and body creme composition described herein provides an easy-to-use and effective topical treatment for common skin ailments such as itchiness, dryness, redness, eczema, and psoriasis without relying on harsh or synthetic ingredients such as tars or alcohols. Topical application of the composition provides immediate relief from symptoms such as itchiness and redness. With regular daily use over a period of days to weeks, the composition described herein provides noticeable reduction in the symptoms of eczema, psoriasis and other chronic skin ailments.

DETAILED DESCRIPTION

In one embodiment, a composition for a hand and body creme is an admixture of almond oil, cocoa butter, jojoba oil, vitamin E oil, a commercially available beeswax derivative, hydrogenated soybean flakes, pure beeswax and vitamin A oil.

In one embodiment, in which the hand and body creme composition has a creamy solid consistency, almond oil contributes from 25% to 35% by volume to the total volume of the composition. Almond oil is a naturally occurring substance which is commonly used in skin and hair care products. It is known as an effective skin conditioner and moisturizer, and is effective as a carrier for other ingredients. A particular advantage of almond oil is that it provides skin conditioning benefits while maintaining low comedogenicity.

Cocoa butter contributes from 18% to 30% by volume to the total volume of the composition. Cocoa butter, derived from the beans of the cocoa plant, is a known skin emollient and conditioner, commonly used in a variety of skin care products. It is used in the hand and body creme composition for its skin conditioning properties and to thicken the consistency of the composition. Cocoa butter is readily commercially available from, for example, health food stores.

Jojoba oil is produced by oil pressing seeds of the jojoba plant which grows in arid desert regions of North America. The oil, actually a liquid wax, has hypoallergenic skin conditioning properties and is believed to have therapeutic benefits. It is commonly used in a wide range of products including cosmetic, skin and hair care products. Jojoba oil is used in the hand and body creme composition for the temporary relief of the symptoms of eczema, dermatitis and psoriasis, and as a carrier for the remaining ingredients. The hand and body cream composition includes from 18% to 28% by volume of jojoba oil. Jojoba oil is commonly commercially available at most health food stores.

Vitamin E is recognized for its skin restorative and healing properties. Vitamin E is used in topical applications for the relief of dry or chapped skin, reduction and elimination of scar tissue, healing of burns and abrasions, and wrinkle reduction. It is commonly available as an oil in varying concentrations of the vitamin measured in International Units (I.U.). For the hand and body creme composition, pure vitamin E oil having a concentration of 28,000 I.U. per ounce is used, but varying concentrations of vitamin E may be used. The hand and body creme composition includes vitamin E oil in an amount from 5% to 10% by volume of the composition. Vitamin E oil is commonly commercially available at most health food stores.

Beeswax derivatives are used in topically applied creams, lotions, cosmetics and soaps. In one embodiment of the hand and body creme composition, a commercially available beeswax derivative is added as a consistency regulator and an emulsion stabilizer, and contributes from 5% to 10% by volume to the composition. One such beeswax derivative suitable for this purpose is Rosswax 2673, commercially available from the Frank B. Ross Co., Jersey City, N.J. Rosswax 2673 is a mixture of beeswax, fatty acids, alcohol and glycerides. Other beeswax derivatives may be used, including siliconal beeswax, PEG-beeswax and hexanediol beeswax.

Hydrogenated soybean flakes are also added as consistency regulators and emulsion stabilizers. They contribute from 2% to 6% by volume to the hand and body creme composition. Soybean flakes are commonly commercially available and may be purchased from, for example, Arista Industries Inc., Darien, Conn.

Pure beeswax is a common ingredient in cosmetic products. Pure beeswax is added to the hand and body creme composition to influence the consistency of the composition and to form a barrier on the skin which impedes water loss. In one embodiment, yellow beeswax is used, but white or yellow beeswax, and beeswax of varying consistencies and plant sources may be used. Beeswax contributes from 2% to 6% by volume of the composition and is readily available at most health food stores.

Vitamin A, in topical applications, is used for the control of chapped or dry skin, and for the temporary relief of minor skin ailments such as burns, abrasions and rashes. It is readily commercially available as an oil which may be purchased from most health food stores. In one embodiment, the vitamin A oil has a vitamin A concentration of 25,000 I.U. per ounce, but the concentration may vary.

In preparing the hand and body creme composition, the cocoa butter, Rosswax 2673 and beeswax are heated to melt and combined at a temperature of about 128° F. to about 132° F. (about 53.3 to about 55.5° C.). While stirring, the hydrogenated soybean flakes are combined with the hot wax mixture. Separately, the almond oil, jojoba oil, vitamin E oil and vitamin A oil are combined at room temperature to form an oil mixture. The oils are combined by introducing them to a common container and stirring or otherwise agitating the mixture for a brief period of at least one minute. The melted wax mixture is then transferred to a blender and blended at high speed of about 11,000 to about 20,000 rpm under vacuum for approximately one minute. The vacuum is formed by an aspirator or vacuum pump connected to the blender, and is applied to prevent air oxidation which may occur during blending.

The oil mixture is then introduced to the wax mixture in the blender and blended at high speed as above, under vacuum, for at least a minute. In one embodiment the oil mixture and wax mixture are blended together for 10 minutes. The mixture is then poured into storage containers and cooled to a room temperature of less than 85° F. for about 30 to about 60 minutes, &depending on the type of containers used. Storage containers may be any type of commonly available container, such as glass or plastic jars, bottles or the like, and the containers may be transparent or opaque. After cooling, the composition is a cream-colored solid with a melting point of about 88° F. to about 92° F. (about 31.1 to about 33.3° C.), and ready to be topically applied for the relief of skin on hands and body.

Alternate embodiments of the hand and body creme composition include the addition of shea butter, water, honey or essential oils to vary the consistency or fragrance of the composition.

Shea butter, also known as karite butter, is a yellowish or ivory-colored paste produced from the shea tree which grows wild in the savannah regions of West Africa. The paste is extracted from the almond-like fruit of the shea tree, and traditionally has been used by West Africans for treatment of skin and scalp ailments. Shea butter has a high content of non-saponifiable fatty acids which make it an excellent moisturizer and skin conditioner. In alternate embodiments of the hand and body creme composition, shea butter is added in amounts of up to 8% by volume of the total volume of the composition. The shea butter is used to modify the consistency of the composition to a more fluid, lotion-like consistency while simultaneously adding skin moisturizing and skin conditioning benefits. Shea butter may be purchased from, for example, health food stores. In embodiments which use shea butter, it is incorporated into the composition by melting with the cocoa butter, Rosswax 2673, hydrogenated soybean flakes and beeswax.

In other embodiments, water is added to vary the consistency of the hand and body creme composition and to accommodate the needs of those consumers with more oily skin. Increased amounts of water increase the fluidity of the composition. Water is added in an amount of up to 5% by volume of the total volume of product. In one embodiment, distilled water is used, but bottled water or commonly available tap water may be used. In embodiments which include water, the water is added and blended in when the oil mixture and hot wax mixture are added together and blended.

In other embodiments, honey is added to the composition in an amount of up to 5% by volume. The honey is added as a moisturizer and consistency regulator. One embodiment includes U.S. Grade A pure clover blend honey, but the grade and plant source of the honey may vary. Commercial sources of honey are commonly known. Honey, if used, is added to the hot wax mixture and blended with the hot wax mixture before blending with the oil mixture.

In still other embodiments of the hand and body creme composition, essential oils from a single or multiple sources are added for a range of fragrances. Essential oils which may be added alone or in combination contribute up to a total of 2% by volume and include, but are not limited to, the following: aniseed, attar of rose, balm, bay rum, benzoin, bergamot, cedar, chamomile, cinnamon, coriander, cumin, cypress, elemi, eucalyptus, fennel, frankincense, geranium, grapefruit, hyssop, immortelle, iris, jasmine, lavender, lemon, lemongrass, lime, mimosa, myrrh, myrtle, narcissus, narde, neroli, niaouli, orange, patchouli, pine, rose, rosewood, sandlewood, tuberose, tumeric, tonka bean, vanilla, verbena, vetiver, violet, yarrow, and ylang-ylang. Essential oils are poured into the blender with the hot wax mixture and oil mixture, and they are all combined in the blender.

In use, the hand and body creme composition is topically applied once or twice a day to external skin areas on the body and hands which are afflicted with dryness, itchiness, eczema, psoriasis or another common skin ailment. Application of a thin film of the hand and body creme composition provides immediate relief from skin discomfort, including itching and dryness. With continued and regular applications over the course of a few days to a week, the hand and body composition as described herein provides therapeutic benefits. Regular use of the hand and body creme composition is particularly effective in ameliorating the scaling, irritation and discoloration of eczema, and is also effective in reducing scarring and hyperpigmentation from blemishes.

EXAMPLE 1

One embodiment of the hand and body creme composition is an admixture of 30 vol. % almond oil, 23 vol. % cocoa butter, 23 vol. % jojoba oil, 7.5 vol. % vitamin E at 28,000 I.U. per ounce, 7.5 vol. % Rosswax 2673, 4 vol. % hydrogenated soybean flakes, 4 vol. % pure beeswax, and 1 vol. % vitamin A oil at 25,000 I.U. per ounce. The resultant composition, when produced according to the method described herein, is a creamy solid.

EXAMPLE 2

Another embodiment of a hand and body creme composition is an admixture of 30 vol. % almond oil, 18 vol. % cocoa butter, 23 vol. % jojoba oil, 7.5 vol. % vitamin E at 28,000 I.U. per ounce, 5 vol. % Rosswax 2673, 4 vol. % hydrogenated soybean flakes, 3 vol. % pure beeswax, 0.5 vol. % vitamin A oil at 25,000 I.U. per ounce, 4 vol. % shea butter, 2.5 vol. % water, and 2.5 vol. % U.S. Grade A pure clover blend honey. The resultant composition has the fluid consistency of a lotion, and is more suitable than a creamy solid embodiment for those having oily skin.

EXAMPLE 3

Twenty human volunteer subjects reporting a range of skin ailments were asked to evaluate the performance of a creamy solid embodiment of the hand and body creme composition over the course of several weeks. The 5 subjects with eczema reported noticeable reduction of eczematous symptoms within 5 days to 2 weeks following regular application of the hand and body creme composition at least once daily. The remaining 15 subjects all reported noticeable relief from skin ailments including dryness, itchiness, discoloration and psoriasis following regular, daily application over a period of 5 days to 1 week.

The hand and body creme composition described herein provides an easy-to-use and effective topical treatment for common skin ailments such as itchiness, dryness, redness, eczema, and psoriasis without relying on harsh or synthetic ingredients such as tars or alcohols. Topical application of the composition provides immediate relief from symptoms such as itchiness and redness. With regular daily use over a period of days to weeks, the composition described herein provides noticeable reduction in the symptoms of eczema, psoriasis and other chronic skin ailments.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

We claim:

1. A composition for a hand and body creme comprising a mixture of
   from about 25% to about 35% by volume of almond oil;
   from about 18% to about 28% by volume of cocoa butter;
   from about 18% to about 28% by volume of jojoba oil;
   from about 5% to about 10% by volume of vitamin E;
   from about 5% to about 10% by volume of beeswax derivative selected from the group consisting of siliconal beeswax, PEG-beeswax, hexanediol beeswax and a mixture of beeswax, fatty acids, alcohol and glycerides;
   from about 2% to about 6% by volume of hydrogenated soybean flakes;
   from about 2% to about 6% by volume of beeswax; and
   from about 0.2% to about 1% by volume of vitamin A.

2. A composition in accordance with claim 1 further comprising from about 0% to about 8% by volume of shea butter.

3. A composition in accordance with claim 1 further comprising from about 0% to about 5% by volume of honey.

4. A composition in accordance with claim 3 wherein said honey comprises U.S. Grade A clover blend honey.

5. A composition in accordance with claim 1 further comprising from about 0% to about 5% by volume of water.

6. A composition in accordance with claim 1 further comprising from about 0% to about 2% by volume of essential oil.

7. A composition in accordance with claim 1 wherein said vitamin E comprises a solution having vitamin E in a concentration of about 28,000 International Units (I.U.) per ounce.

8. A composition in accordance with claim 1 wherein said vitamin A comprises a solution having vitamin A in a concentration of about 25,000 International Units (I.U.) per ounce.

9. A method for preparing a hand and body creme composition from almond oil, cocoa butter, jojoba oil, vitamin E oil, a beeswax derivative, hydrogenated soybean flakes, beeswax and vitamin A oil, said method comprising the steps of:
   melting the cocoa butter, beeswax derivative and beeswax;
   combining the melted cocoa butter, melted beeswax derivative and melted beeswax to form a hot wax mixture;
   adding hydrogenated soybean flakes to the hot wax mixture while stirring;
   blending the hot wax mixture at high speed under a vacuum;
   separately forming an oil mixture by combining almond oil, jojoba oil, vitamin E oil and vitamin A oil;
   adding the oil mixture to the hot wax mixture to form a hot composition;
   blending the hot composition at high speed under a vacuum; and
   cooling the hot composition wherein the beeswax derivative is selected from the group consisting of siliconal beeswax, PEG-beeswax, hexanediol beeswax and a mixture of beeswax, fatty acids, alcohol and glycerides.

10. A method in accordance with claim 9 further comprising the step of pouring the hot composition into opaque storage containers.

11. A method in accordance with claim 9 wherein the composition includes almond oil present in amount from about 25 vol. % to about 35 vol. %, cocoa butter present in amount from about 18 vol. % to about 28 vol. %, jojoba oil present in amount from about 18 vol. % to about 28 vol. %, vitamin E oil present in amount from about 5 vol. % to about 10 vol. %, a beeswax derivative present in amount from about 5 vol. % to about 10 vol. %, hydrogenated soybean flakes present in amount from about 2 vol. % to about 6 vol. %, beeswax present in amount from about 2 vol. % to about 6 vol. %, and vitamin A oil present in amount from about 0.2 vol. % to about 1 vol. %.

12. A method in accordance with claim 11 wherein the composition further comprises shea butter, the shea butter being present in an amount up to about 8 vol. %, said method further comprising the steps of:

melting the shea butter; and adding the melted shea butter to the hot wax mixture.

13. A method in accordance with claim 11 wherein the composition further comprises honey, the honey being present in amount up to about 5 vol. %, said method further comprising the step of stirring the honey into the hot wax mixture.

14. A method in accordance with claim 11 wherein the composition further comprises water, the water being present in amount up to about 5 vol. %, and wherein forming an oil mixture comprises combining the water with the almond, oil, jojoba oil, vitamin E oil and vitamin a oil in a common container.

15. A method in accordance with claim 11 wherein the composition further comprises essential oil, the essential oil being present in amount up to about 2 vol. %, and wherein forming an oil mixture comprises combining the essential oil with the almond oil, jojoba oil, vitamin E oil and vitamin a oil in a common container.

16. A method in accordance with claim 11 wherein the step of blending the hot wax mixture at high speed under a vacuum in the blender comprises connecting a vacuum pump to the blender.

17. A method for preparing a hand and body creme composition from almond oil, cocoa butter, jojoba oil, vitamin E oil, a beeswax derivative, hydrogenated soybean flakes, beeswax and vitamin A oil, said method comprising the steps of:

melting the cocoa butter, beeswax derivative and beeswax;

combining the melted cocoa butter, melted beeswax derivative and melted beeswax at a temperature of about 128° F. to about 132° F. to form a hot wax mixture;

adding hydrogenated soybean flakes to the hot wax mixture while stirring;

blending the hot wax mixture at high speed under vacuum for about one minute;

separately forming an oil mixture by combining almond oil, jojoba oil, vitamin E oil and vitamin A oil;

adding the oil mixture to the hot wax mixture to form a hot composition;

blending the hot composition at high speed under vacuum for up to about 10 minutes; and cooling the hot composition to a temperature of less than about 85° F. wherein the beeswax derivative is selected from the group consisting of siliconal beeswax, PEG-beeswax, hexanediol beeswax and a mixture of beeswax, fatty acids, alcohol and glycerides.

* * * * *